(12) United States Patent
Khan (10) Patent No.: US 8,579,841 B2
(45) Date of Patent: Nov. 12, 2013

(54) BLOOD CLOT PREVENTION DEVICE

(76) Inventor: Sitara R. Khan, Old Westbury, NY (US)

( * ) Notice: Subject to any disclaimer, the term of this patent is extended or adjusted under 35 U.S.C. 154(b) by 478 days.

(21) Appl. No.: 12/734,106

(22) PCT Filed: Oct. 9, 2008

(86) PCT No.: PCT/US2008/079431
§ 371 (c)(1),
(2), (4) Date: Jun. 28, 2010

(87) PCT Pub. No.: WO2009/049103
PCT Pub. Date: Apr. 16, 2009

(65) Prior Publication Data
US 2010/0268130 A1    Oct. 21, 2010

Related U.S. Application Data

(60) Provisional application No. 60/978,730, filed on Oct. 9, 2007.

(51) Int. Cl.
*A61H 7/00* (2006.01)
*A61H 9/00* (2006.01)

(52) U.S. Cl.
USPC ............ 601/149; 601/148; 601/150; 601/152

(58) Field of Classification Search
USPC ...................... 601/15, 148–152; 606/201–203
See application file for complete search history.

(56) References Cited

U.S. PATENT DOCUMENTS

| | | | | |
|---|---|---|---|---|
| 3,862,629 A * | 1/1975 | Rotta | ............................. | 601/150 |
| 4,029,087 A * | 6/1977 | Dye et al. | ....................... | 601/152 |
| 5,135,282 A * | 8/1992 | Pappers | ....................... | 297/284.3 |
| 6,706,246 B2 * | 3/2004 | Hopkins et al. | ............. | 423/239.1 |
| 6,786,879 B1 * | 9/2004 | Bolam et al. | ................... | 601/152 |
| 7,044,924 B1 * | 5/2006 | Roth et al. | ....................... | 601/151 |
| 7,074,177 B2 * | 7/2006 | Pickett et al. | .................... | 600/17 |
| 7,618,384 B2 * | 11/2009 | Nardi et al. | .................... | 601/149 |
| 2003/0195441 A1 * | 10/2003 | Firouzgar | ........................ | 601/46 |
| 2005/0131273 A1 * | 6/2005 | Asano et al. | ..................... | 600/27 |
| 2005/0154336 A1 * | 7/2005 | Kloecker et al. | ............... | 601/148 |
| 2006/0069325 A1 * | 3/2006 | Inada et al. | ......................... | 601/2 |
| 2006/0270952 A1 * | 11/2006 | Freeman et al. | ................. | 601/41 |

* cited by examiner

*Primary Examiner* — Justine Yu
*Assistant Examiner* — Douglas Sul
(74) *Attorney, Agent, or Firm* — Thomas A. O'Rourke; Bodner & O'Rourke, LLP (57) ABSTRACT

An adjustable pressure cuff device is provided for the arm or leg of a user for stimulating blood flow and preventing blood clots. The pressure cuff contains a number of bladders which wrap in the direction of the cuff and which are arranged in succession down the arm or leg of a user. An air compressor is connected to the bladders via a multiplicity of tubes, each of which contain a valve. A control module runs the air compressor and sequentially opens the valves to provide air pressure to the bladders in succession along the arm or leg of a user. Further, between the bladders and the valves, additional tubes containing valves are provided to equalize pressure between bladders before exhausting the air from a previously pressurized bladder to save power and allow for increased patterns of bladder pressure. The pressure levels and bladder dwell times may be adjusted by the user or based on predetermined settings. Optionally, the device provides electrical stimulation, pulsations, heating, and cooling.

22 Claims, 12 Drawing Sheets

BLOOD CLOT PREVENTION DEVICE

CROSS REFERENCE TO RELATED APPLICATIONS

This application claims priority to U.S. Provisional Application Ser. No. 60/978,730, filed Oct. 9, 2007, entitled "Blood Clot Prevention Device." The contents of which are incorporated herein by reference in its entirety.

FIELD OF THE INVENTION

The present invention generally relates to pressure cuffs, and more specifically to a pressure cuff with multiple pressure bladders.

BACKGROUND

There appears to be a link between extended periods of immobility in confined quarters, such as a person might experience on a long journey in an airplane or other vehicle, and the occurrence of Deep Vein Thrombosis (DVT) or the formation of blood clots in the lower extremities of an individual. Further, extended periods of immobility may aggravate other conditions such as arthritis, various neuropathies, swelling, lymphedema, fibromyalgia, tension headaches, and other bone and muscle injuries.

While several factors, such as advanced age, a persons weight, and other health characteristics may increase or decrease the likelihood of DVT occurring, extended periods of immobility, are a likely cause of DVT occurring in the legs. If a person does suffer from DVT, a potentially fatal blood clot could form which may be large enough that the clot does not naturally dissolve. Such a clot may break loose and travel from the person's leg to their heart or lungs resulting in serious illness or even death.

While numerous treatment and preventative strategies exist, the most common way of avoiding the occurrence of DVT is to exercise the legs by flexing the leg muscles or simply getting up and briefly walking around perhaps once an hour or more if possible. The action of walking stimulates blood flow by causing contracting muscles to pump the blood onward through the legs. Unfortunately, under many circumstances a persons mobility may be limited to such an extent that walking around is not possible or is undesirable, for example while on a plane. In addition to airline travel there may be a link between DVT and other conditions where people are required or choose to sit for long periods of time such as when driving, working at a desk or assembly line, watching television in their home, etc.

Thus, it is desirable to stimulate blood flow in a person with restricted mobility, particularly when in airplanes, trains, cars, etc., to prevent the formation of blood clots and to relieve various other conditions.

SUMMARY OF THE INVENTION

In order to stimulate blood flow and prevent the formation of blood clots, a pressure cuff containing a series of bladders is worn on the arm or leg of a user and is adjustable to fit different users at different points of the arm or leg, e.g., by using a hook and latch fastener, a hook and loop fastener, or any other type of fastener that can secure the cuff to a user. Each of the bladders is connected to an air compressor by a tube containing a valve. The air compressor and valves are operated by a control module powered by a power source. The control module runs the air compressor and opens the valves in succession to pressurize the bladders one after another along the arm or leg of a user. Different pressure levels and different dwell times are contemplated and more than one bladder may be pressurized at any single point in time. The bladders are inflated and deflated to pressures optimized for each condition being treated. Additional tubes containing valves may also be provided to connect two bladders and equalize pressure levels therebetween. In this way, a previously fully pressurized bladder may be used to partially pressurize another bladder in order to save power and provide intermediate pressure levels. An exhaust port containing an exhaust valve is connected to the tubes to depressurize bladders as desired. The control module manages the duration of operation of the air compressor and the timing of the opening of the valves so that the pressure levels and dwell times may be preprogrammed or adjustable by the user, e.g., into different wave-like patterns along the arm or leg of a user.

DETAILED DESCRIPTION OF THE CERTAIN EMBODIMENTS

Figure 1:
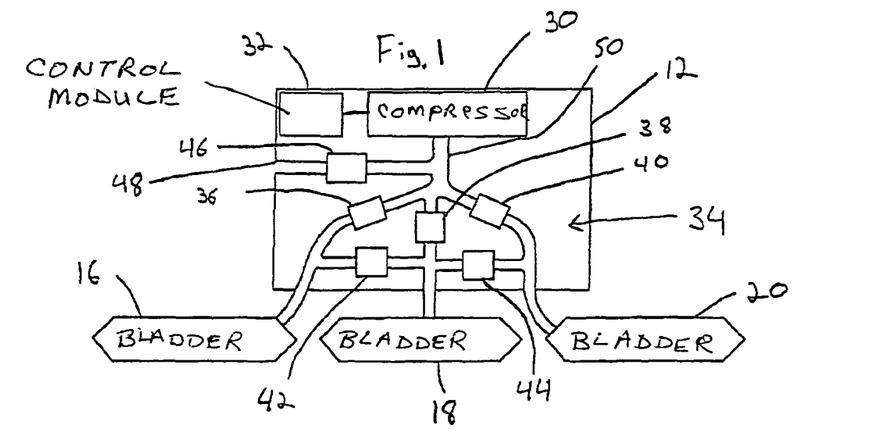
FIG. 1 is a schematic view of a control unit and bladders according to an embodiment of the present invention.
Figure 2:
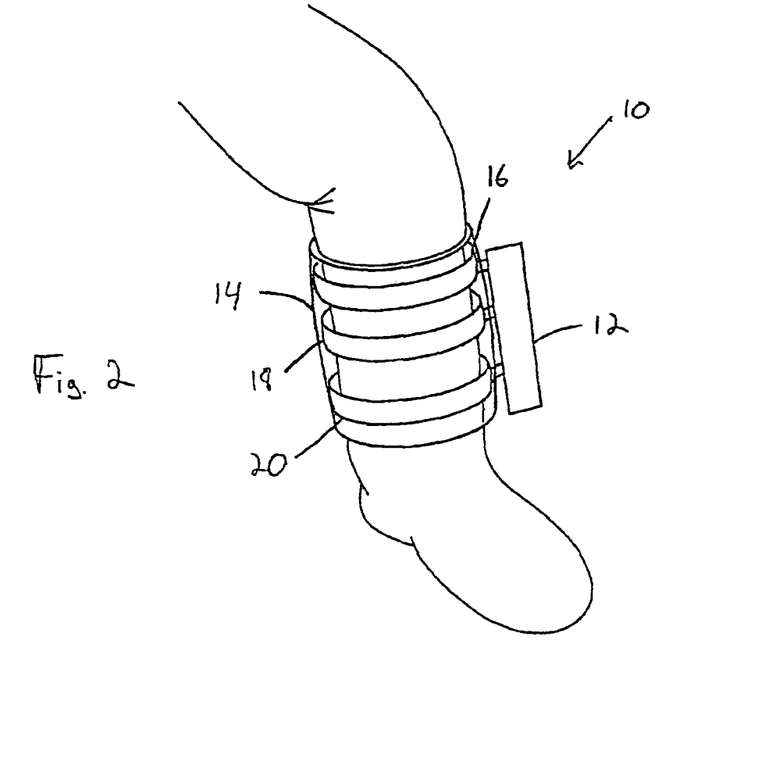
FIG. 2 is a perspective view of the pressure cuff device according to an embodiment of the present invention on the leg of a user.
Figure 13:
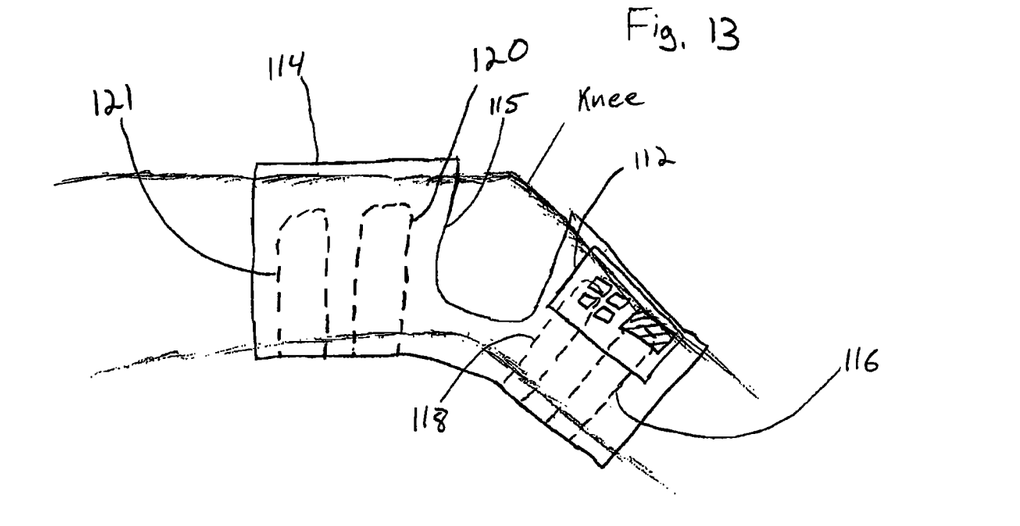
FIG. 13 is a perspective view of the pressure cuff of FIG. 11 on the knee of a user according to an embodiment of the present invention.

Referring now to FIGS. 1 and 2, the pressure cuff device 10 for the prevention of the formation of blood clots comprises a pressure cuff control unit 12 and a cuff 14 attached thereto. The cuff 14 is sized so as to fit around the calf area of the leg of a user. Within the cuff 14 are disposed three or more pressure bladders 16, 18, and 20. Thus FIG. 1 shows a cuff having three bladders, alternative embodiments may include any number of bladders. The three pressure bladders 16, 18, and 20 extend substantially around the circumference of the user's leg and are arranged along the length of the user's leg. The bladders can also be dimensioned and positioned within the cuff 14 such that the bladders only extend around approximately two-thirds of the circumference of the back portion of the user's leg, for example as shown in FIG. 13. Thus, the bladders will be positioned to inflate and press against the muscular calf portion of the user's leg, and not the shin bone located in the front portion of the leg. Therefore, the volume of the bladders can be reduced while not significantly reducing their effectiveness to cause blood to move within the user's leg. In addition, the bladders can be sized so that when inflated, adjacent bladders are in relatively close proximity to each other or are touching. Thus, the bladders can act upon a continuous region of the leg.

The cuff 14 is placed on the leg such that lower bladder 20 is closest to the user's ankle region when worn. The cuff 14 can include hook and loop type fastening strips 64, such as that available under the common trade name Velcro®, to secure the cuff around the user's limb.

Referring now to FIG. 2, the pressure cuff control unit 12 comprises a rechargeable power source and control module 32, an air compressor 30, and a network of tubing and valves 34. Although a rechargeable power source is preferable, the pressure cuff can be powered by any power source. Possible power sources may include line AC power, disposable batteries, etc. The air compressor 30 is connected to the network of tubing 50 such that when operating, the compressor 30 forces compressed air through the tubing 50. A number of valves 36, 38, 40, 42, 44, and 46 are connected inline with the tubing 50 and can be individually opened and closed to control the direction of flow of compressed air through the tubing 50. It is contemplated that valves 36, 38, 40, 42, 44, and 46 are normally-closed solenoid valves, which are opened when energized and closed when not energized, but other types of valves are also contemplated. As shown in FIG. 2, all the valves, compressors, and other electrical components to drive the pressure bladders can be located within the pressure cuff control unit 12, thus eliminating the need to place these components within the cuff 14, which increases user comfort and safety. The device can be designed such that only the pressure tubing communicates between the cuff 14 and the control unit 12. The control unit 12 has a housing, which acts as a protective barrier to protect the user of the device from heat and electrical shock and other hazards to ensure the safety of the user.

The control module 32, which can include a suitable microprocessor, memory, programming and other circuitry, controls the operation of the compressor 30 and the valves 36, 38, 40, 42, 44, and 46 such that air pressure in the bladders 16, 18, and 20 can be sequentially varied with minimal operation of the compressor 30. Valves 36, 38, and 40 individually control fluid communication between compressor 30 and bladders 16, 18, and 20 respectively. Valves 42 and 44 control fluid communication between the respective bladders. Valve 46 controls fluid communication between the compressed air system and the external environment, which allows air pressure within bladders 16, 18, and 20 to be exhausted.

The bladders 16, 18, and 20 can be filled at various times. The bladders can be inflated in order from the most distal bladder (lowest on the leg) to the most proximal bladder (highest on the leg), and vice versa.

For example, in one mode of operation, the control module 32 controls the opening and closing of valves such that when a first bladder is filled with air at a high pressure, at least a portion of that high pressure air can be vented into a next bladder. Thus, the pressure in a second bladder can be changed without operating the compressor. In this way, power consumption by the compressor can be reduced, while using at least a portion of the high pressure air in a first bladder to fill a second bladder to an intermediate pressure.

In one, first exemplary operation, control module 32 sends an electrical signal to compressor 30, which causes the compressor 30 to compress air through tubing 50. At the same time, control module 32 sends an electrical signal to energize normally-closed control valve 36, causing it to open. Thus, fluid communication between compressor 30 and bladder 16 is established and compressed air can pass into bladder 16, causing it to inflate. The bladder 16 is filled until a predetermined pressure is reached. For purposes of illustration only and not intended to be limiting, bladder 16 is filled until a pressure of 100 mmHg or "full pressure" is reached. However, the filling pressure of the bladders can be varied and other pressures are contemplated.

Once bladder 16 is filled to the predetermined pressure, the control module 32 causes the valve 36 to de-energize and close and for the compressor 30 to turn off. With the valve 36 in the closed position, the pressure is maintained in bladder 16. The pressure in bladder 16 is maintained for a predetermined period of time.

After the pressure in bladder 16 is maintained for the predetermined period of time, the control module 32 sends an electrical signal to normally-closed valve 42 causing it to energize and open. Once valve 42 is in the open position, fluid communication is established between bladder 16 and 18. Thus, the pressure in bladder 16, which was previously pressurized by compressor 30 as discussed above, and bladder 18 is substantially equalized. For purposes of illustration only and not intended to be limiting, bladder 16 and bladder 18 have approximately equal volumes. However, the volumes of the bladders do not have to be equal and bladders of various volumes are contemplated.

With the pressure between bladders 16 and 18 substantially equalized and the volumes of the bladders being approximately equal, the pressure in bladders 16 and 18 is approximately half the pressure that was in bladder 16 before actuation of valve 42, or approximately 50 mmHg (100 mmHg/2=50 mmHg) or "half pressure." Once the pressure is equalized between bladders 16 and 18, the control module 32 causes the valve 42 to de-energize and close. With the valve 42 in the closed position, the pressure is maintained in bladders 16 and 18. The pressure in bladders 16 and 18 is maintained for a predetermined period of time.

After the pressure in bladders 16 and 18 is maintained for the predetermined period of time, the control module 32 sends an electrical signal to normally-closed valves 36 and 46 causing them to open. With valves 36 and 46 in the open position, fluid communication is established between bladder 16 and exhaust port 48 and the ambient environment. Thus, the remaining air pressure in bladder 16 is reduced as the pressurized air in bladder 16 is exhausted to the ambient environment. The relative pressure of bladder 16 is reduced to zero or "zero pressure." However, valve 42 is not energized and thus remains closed, which maintains the pressure in bladder 18 during this process.

Once the relative pressure in bladder 16 is reduced to zero, the control module 32 causes the valves 36 and 46 to de-energize and close. The "zero pressure" condition in bladder 16 and the "half pressure" condition in bladder 18 is maintained for a predetermined period of time.

After the half pressure condition has been maintained in bladder 18 for the predetermined period of time, control module 32 sends an electrical signal to energize and open valve 38 and to turn on the compressor 30. Thus, fluid communication is established between compressor 30 and bladder 18. Compressor 30 fills bladder 18 with pressurized air, raising the pressure of bladder 18 from "half pressure" to "full pressure." Since the bladder 18 was already at half pressure from the previous equalization with the full pressure bladder 16, the compressor 30 does not have to be run for as long as it would take to raise bladder 18 from zero pressure to full pressure. Thus, the compressor can be run for a shorter duration.

Once bladder 18 reaches full pressure, the control module de-energizes valve 38 to close it and the compressor 30 is turned off. With the valve 38 in the closed position, the pressure can be maintained within bladder 18 for a predetermined time period.

As can be seen in FIG. 2, bladders 18 and 20 are connected in a similar fashion as bladders 16 and 18 so that the process of equalizing the pressure between bladders 18 and 20, exhausting bladder 18, and filling bladder 20 to full pressure can be achieved by operating the respective valves and the compressor in a similar manner as discussed above with respect to bladders 16 and 18.

After bladder 20 has been maintained at full pressure for the predetermined time period, the bladder 20 can be emptied by opening valves 40 and 46. Also, bladder 20 can be in fluid communication with bladder 16 controlled by an additional normally-closed valve to equalize the pressure between bladders 20 and 16.

The process of successively filling bladders 16, 18, and 20 can be repeated a number of times. This results in a massaging of the user's leg which prevents blood from settling. The inflation of the bladders rhythmically stimulates blood flow, which can help reduce the risk of blood clots forming.

Alternative embodiments of the pressure cuff include other mediums to pressure the bladders 16, 18, and 20. For example, a pump may be used in place of the air compressor to supply a liquid to pressurize the bladders. Furthermore, other gases or substances may be used to pressurize the bladders 16, 18, and 20.

Figure 4:
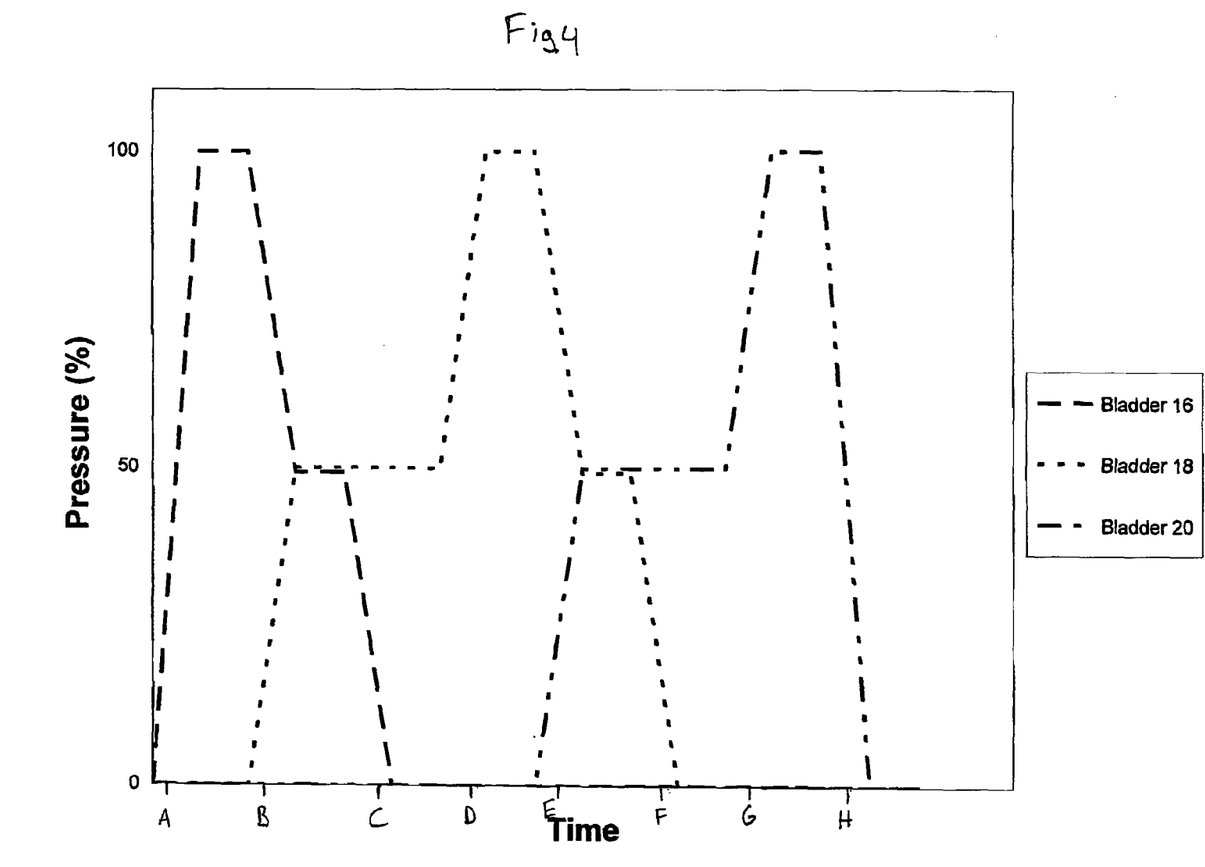
FIGS. 4-8 are charts illustrating exemplary pressure levels and dwell times for the bladders in accordance with various embodiments of the present invention.

FIG. 4 shows a chart that illustrates a first inflation profile of the bladders 16, 18, and 20. This inflation profile generally corresponds to the first exemplary operation described above. The areas referenced A through H on the chart reference some of the different operational conditions of the compressor, valves, and bladders of the pressure cuff device 10. For example, at A, valve 36 is open and compressor 30 is filling bladder 16 from "zero" pressure to "full" or 100% pressure. At B, valve 42 is open and the pressure between bladders 16 and 18 is equalizing. At C, valves 36 and 46 are open and the pressure in bladder 16 is being bled-out to the outside environment. At D, valve 38 is open and compressor 30 is filling bladder 18 from "half" or 50% pressure to full pressure. At E, valve 44 is open and the pressure between bladders 18 and 20 is equalizing. At F, valves 38 and 46 are open and the pressure in bladder 18 is being bled-out to the outside environment. At G, valve 40 is open and compressor 30 is filling bladder 20 from "half" or 50% pressure to full pressure. At H, valves 40 and 46 are open and the pressure in bladder 20 is being bleed-out to the outside environment.

Figure 6:
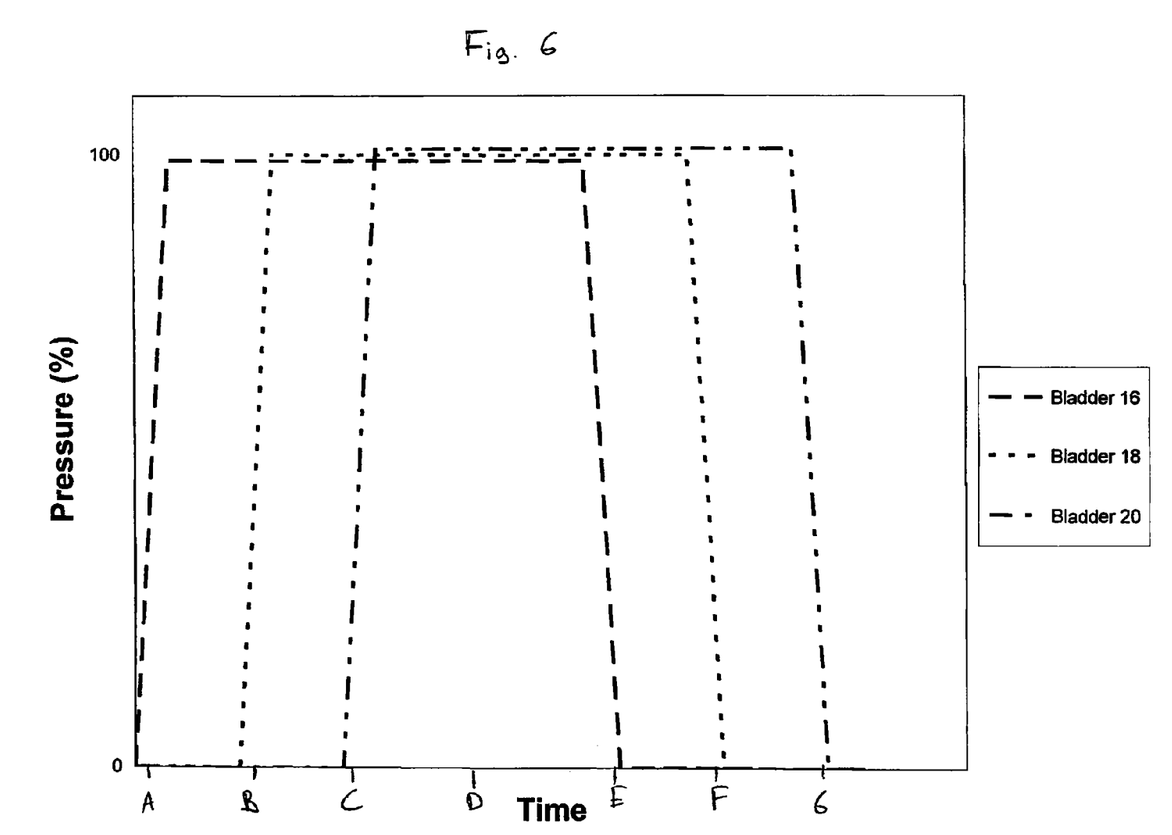

Other inflation patterns of the bladders are also contemplated. For example, FIG. 6 represents a relatively more simplistic inflation profile. At A, valve 36 is open and compressor 30 is filling bladder 16 from zero to 100% pressure. At B, valve 38 is open and compressor 30 is filling bladder 18 from zero to 100% pressure. At C, valve 40 is open and compressor 30 is filling bladder 20 from zero to 100% pressure. At D, all the valves are closed and bladders 16, 18, and 20 are maintained at a 100% pressure for a predetermine dwell time. At E, valves 36 20 and 46 are open and the pressure in bladder 16 is being bled-out to the outside environment. At F, valves 38 and 46 are open and the pressure in bladder 18 is being bled-out to the outside environment. At G, valves 40 and 46 are open and the pressure in bladder 20 is being bled-out to the outside environment.

Figure 5:
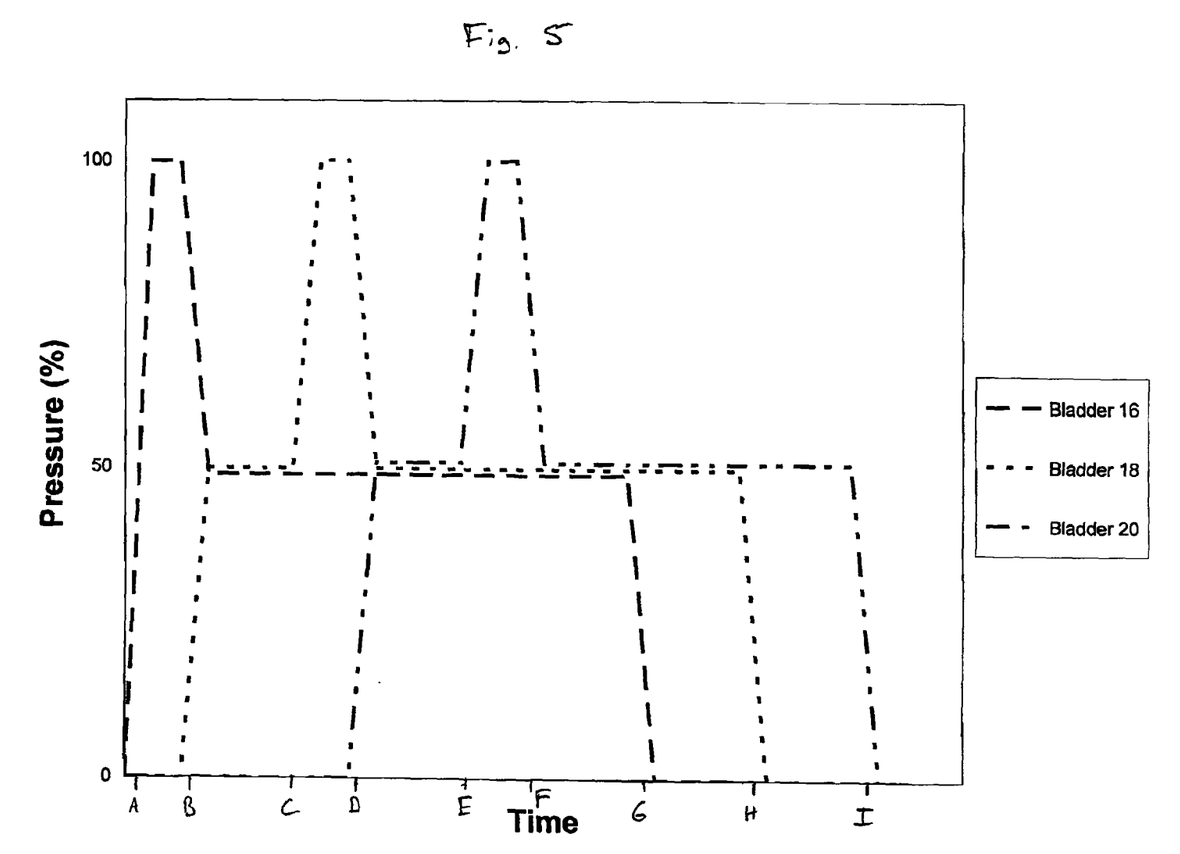
Figure 7:
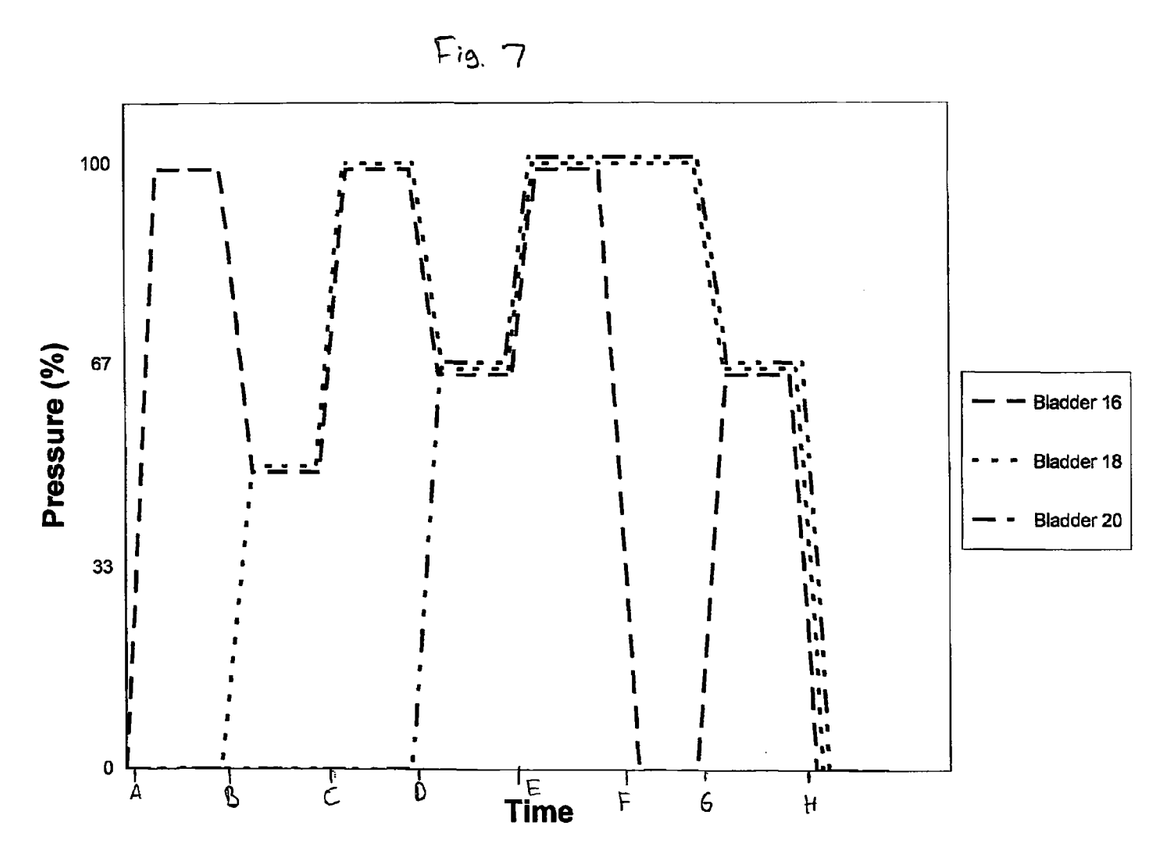
Figure 8:
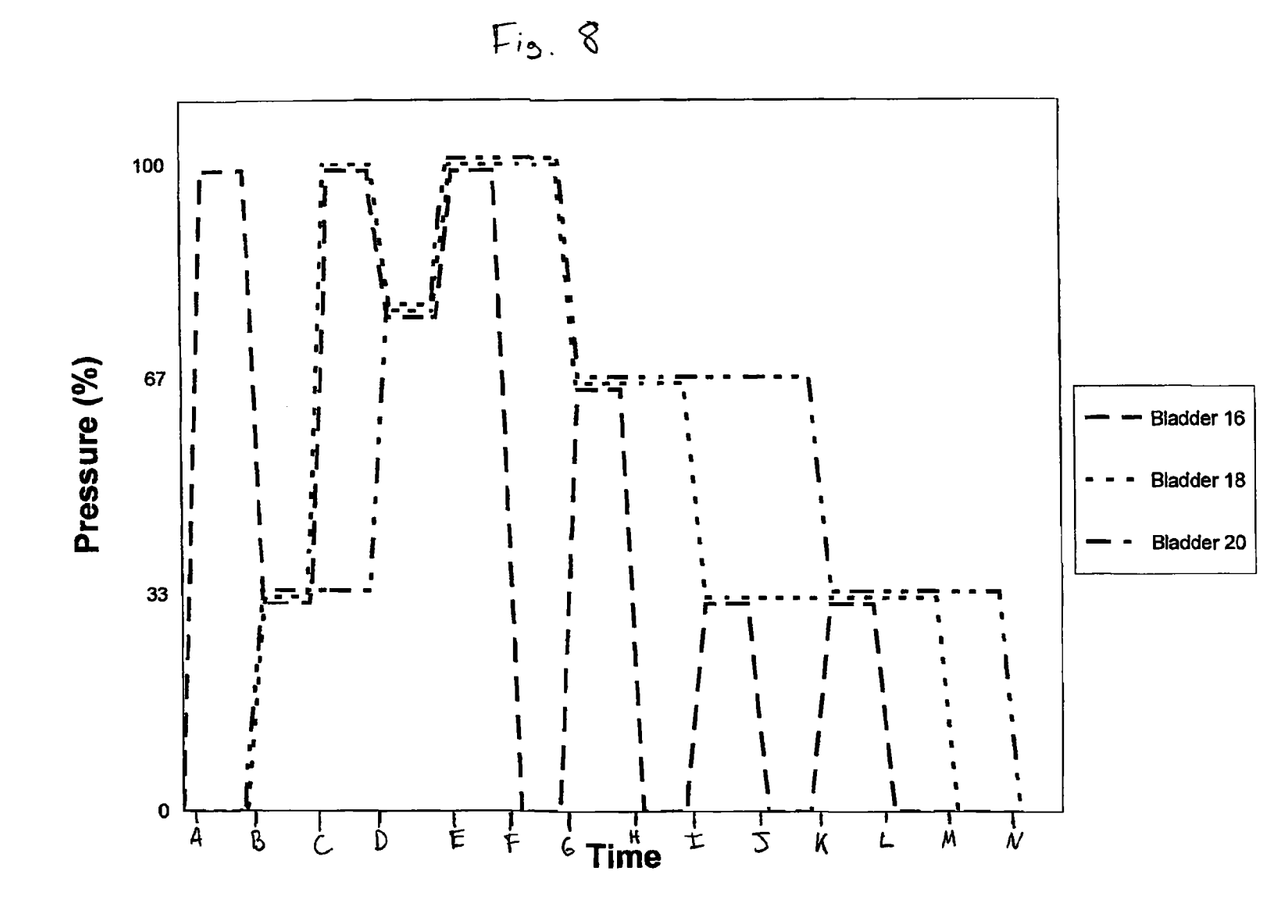

FIGS. 5, 7, and 8 represent relatively more complex inflation profiles. Notably, these more complex inflation profiles can be achieved with only three periods of operation of the compressor 30. For example, the compressor 30 is only operating to fill the bladders at A, C, and E in FIG. 5; at A, C, and E in FIG. 7; and at A, C, and E in FIG. 8. The other pressure changes in the bladders represented in FIGS. 5, 7, and 8 can be achieved by operation of the valves to either equalize the pressure between bladders 16, 18, and 20 or to bleed-out pressure in bladders 16, 18, and 20 to the outside environment in various combinations and at different points in the operation cycle of the pressure cuff device 10.

The charts contained in FIGS. 4-8 are for illustrative purposes and are not necessarily to scale.

A power source is included, which can be in the form of a rechargeable 9 volt battery or other suitable rechargeable or disposable battery. Since the compressor 30 is only operated for a limited duration of the inflation and deflation cycle of the bladders, the rechargeable battery source can provide sufficient power to drive the device for a prolonged period of time. Thus, the device can be used for the duration in which the user is seated, for example, for the duration of a trip in a plane, train, bus, car, or other vehicle or other instance of prolonged inactivity. In addition to the rechargeable battery, the pressure cuff device 10 can include an electrical power adaptor so that pressure cuff device 10 can be plugged into an electrical socket, which can run the device and/or recharge the rechargeable battery. The device can have a rapid recharge feature. The electrical power adaptor is adapted so that the device can be connected to an 110/220 volt power source or to a cigarette lighter socket (e.g., a car cigarette lighter socket). Thus, the pressure cuff device 10 can be used in travel or at home using the rechargeable batteries or the electrical power adaptor during prolonged periods of immobilization and inactivity. The electrical power adaptor can be plugged into the pressure cuff control unit 12 at receptacle 65.

Figure 10:
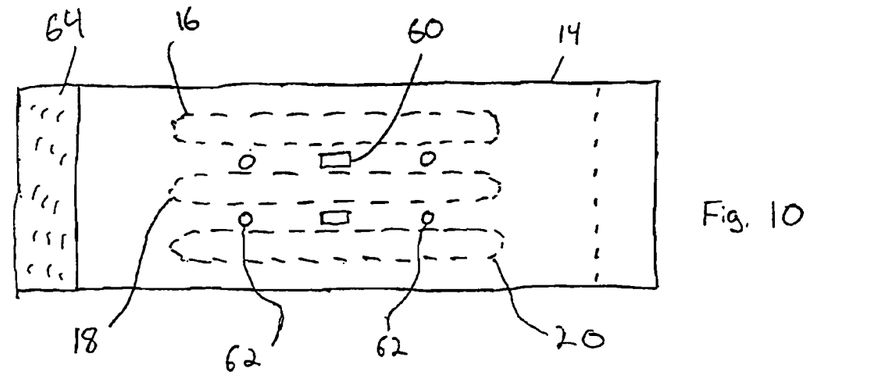
FIG. 10 is a front view of the pressure cuff showing a hook and loop fastener and other features in accordance with an additional embodiment of the present invention.

As shown in FIG. 10, the cuff 14 may include vibration devices or motors 60 and electrical contacts 62. The vibration devices 60 can be controlled by the control module 32 to cause vibration in the leg of the user, thus providing massage. The control module 32 can also cause small electrical pulses to be sent to contacts 62 to cause electrical stimulation and/or contraction of the muscles of the user. The vibration devices 60 and electrical contacts 62 can be provided along the length of the cuff 14 and can be individually controlled so that stimulation can be provided regionally. In additional, electrical heating elements can also be incorporated into the cuff 14 to heat the muscles. Cooling elements can also be incorporated. Further, other types of stimulation and features can be incorporated. This may include light, pulsations, waves, etc. Also, as can be seen in FIG. 10., the cuff 14 can include a hook and loop type fastener system 64, or any other type of fastening mechanism that can secure the cuff 14 to the user.

Figure 3:
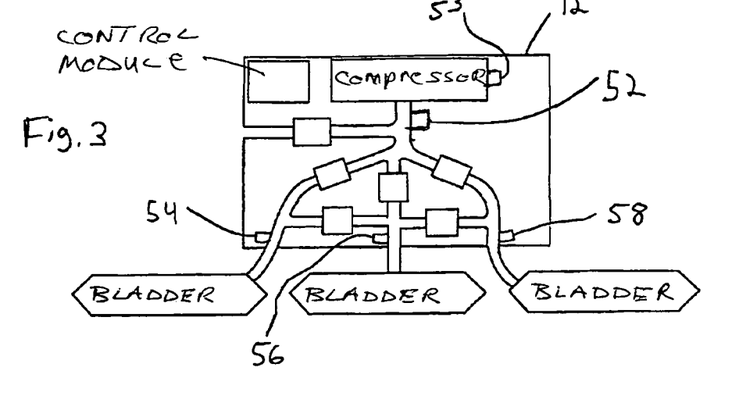
FIG. 3 is a schematic view of the control unit and the bladders in accordance with an additional embodiment of the present invention.

As shown in FIG. 3, pressure sensors 54, 56, and 58 may be included to sense the pressure in the respective bladders and communicate signals relating to the sensed pressure to control module 32. A heating and/or cooling unit 52 may be included to heat or cool the air entering the bladders, thus heating or cooling the leg of the user. Further, thermal sensors 53 may be included to detect an over-heat condition to protect the user's safety, at which point the device can be mechanically and electrically shut down.

Figure 9:
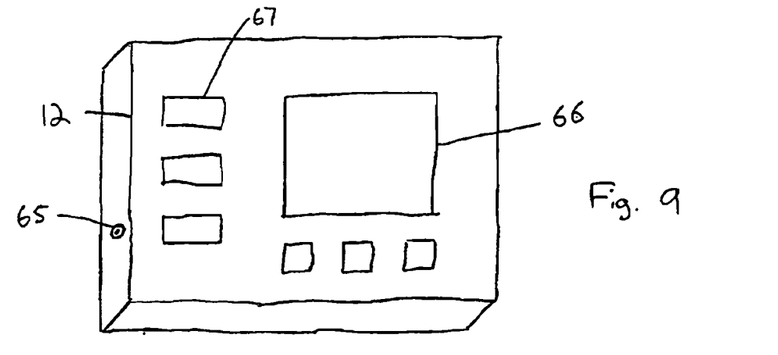
FIG. 9 is a perspective view of the control unit according to an embodiment of the present invention.

The pressure cuff control unit 12 also includes a user interface, as shown in FIG. 9. The user interface includes a display 66, which can be, for example, an LCD display screen or any other suitable type of display screen, and a plurality of buttons and controls 67. The pressure cuff device 10 can come preset with factory settings for inflation pressure, inflation speed, inflation dwell times, and inflation cycle times, which can be pre-programmed into control module 32. The user can select among the various factory settings in order to suit the user's preferences. For example, the user can select between high, medium, and low pressure settings and fast and slow inflation and inflation cycle times. Further, the pressure in the individual bladders can be controlled so that different bladders within the cuff can be filled to different pressures and can be set be the user. The device can have a factory preset default maximum inflation pressure, for example, of 60 mmHg, which the user can adjust as desired.

Further, the device can have preset factory inflation profiles which can include, as a non-limiting example, the inflation profiles shown in FIGS. 4-8. In addition, the user may choose custom settings, wherein the user can select and scale up or down the operational parameters (pressure, time, etc.) as desired. Further, the user can create their own inflation profiles as desired. Inflation profiles may even be synchronized to music, providing a further therapeutic experience.

The interface will allow the user to turn the device on and off, individually control the use, intensity, and operational profiles of all the stimulatory features (pressure, heat, cool, vibration, electrical stimulation, muscle pulsation, etc.), and select between a normal operation or battery saving mode. In battery saver mode, only limited features are operable, for example the user can only use the pressure stimulation and not the other features such as heat and vibration, which helps to conserve power. Using the buttons 67 and the interface, the user can control the features of the device. Thus, the device can be run with pressure, heat, vibration, etc., or any combination of these stimulatory features of the device. Further, the device does not always have to be run in pressure mode with the bladders 16, 18, and 20 inflating and deflating. Rather, only heat, or only vibration can be applied for different stimulatory effects. Also, the interface can include a battery charge indicator to indicate the power level of the batteries, which can be displayed on the display screen 66. The battery charge indicator can also be in the form of a series of sequential lights (e.g., red, yellow, green) to indicate the strength of the battery.

The pressure cuff device 10 can also be controlled by a remote control unit. The device can also be controlled by other peripheral devices, such as a portable digital music player or a personal digital assistant. Thus, the user can remotely control the operation of the device. The remote control unit, which can communicate with pressure cuff control unit 12 via infrared or radio frequency signals for example, is designed to transmit so as not to interfere with the communication between first and second devices when multiple devices are being used on multiple appendages of the user, or when another user of a separate pressure cuff device 10 is in close proximity.

The cuff 14 can be made available in various size and configurations. The cuff 14 can be made having various circumferential dimensions, thus providing different sizes for individuals having different body sizes. The cuff 14 can be made adjustable, for example, using straps, hook and loop type strips, belts, or other fasteners so that its size can be adjusted to fit a particular user. The cuff 14 can also be placed at different positions on the user's leg, including the ankle, calf, over the knee, or around the thigh. The cuff 14 can be provided in different lengths as well to provide coverage to just the calf of a user, the calf and ankle, or it can extend from the ankle to the thigh, for example. As the length of the cuff 14 is increased, additional bladders can be included so that there can be finer control of the pressure over the various regions of the leg. Further, the cuff 14 is not limited to being placed around a user's leg, but can be placed over other body cites and appendages of the user, including the arm and shoulder regions.

The cuff 14 can be made from an elastic fabric material to maintain the position of the cuff 14 on the user and prevent it from falling down. The pressure cuff device 10 can be worn over a user's clothing or under the clothing and in direct contact with the user's skin. Further, the pressure cuff device 10 may be incorporated into a stocking or sock the can be worn by the user. For example, a sock or stocking portion can extend from the bottom of the cuff 14. The user's leg could be inserted through the cuff 14 and the sock portion and pulled up until the cuff 14 was around the desired portion of the user's leg (e.g. the calf). The sock or stocking portion helps maintain the cuff 14 in position on the user's leg.

Further, a user may use two pressure cuff devices 10, one for each leg. The devices are provided with communication modules, for either wired or wireless communication between the two devices. In such a case, one device controls the operation of the other. Thus, the functioning of the devices can be synchronized. The inflation of the bladders in the cuffs can be done in either series or parallel.

In other embodiments, check valves are provided between the individual bladders. Thus, as a first bladder is filled and it reaches a first pressure, one of the check valves opens and establishes fluid communication between a second bladder. Thus, the bladders can be filled in a cascading fashion. The check valves can be simple mechanical valves and can be of the spring biased type.

Figure 11:
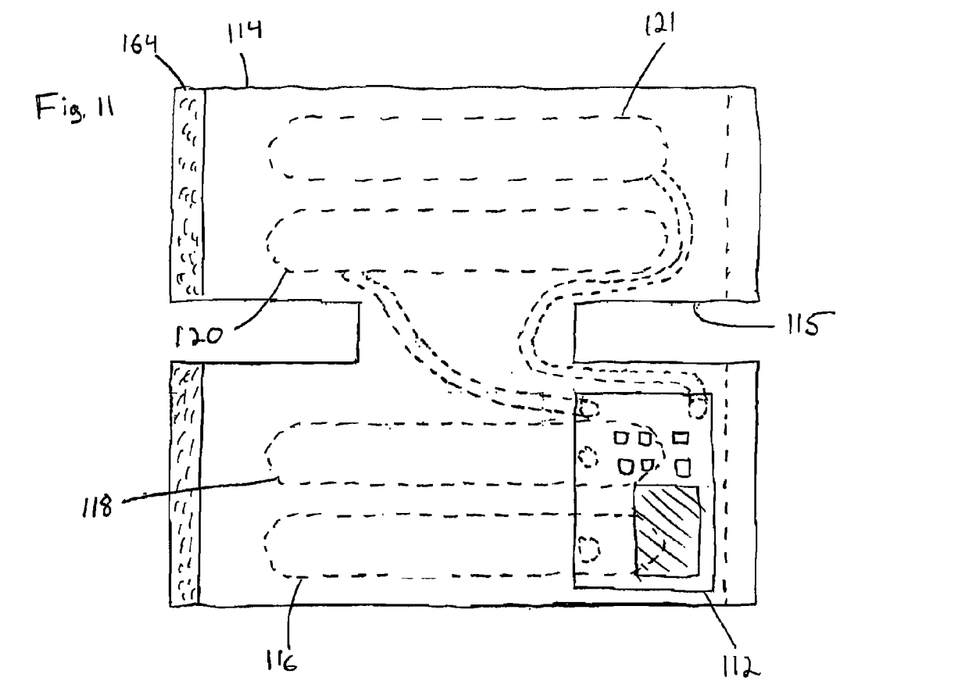
FIG. 11 is a front view of the pressure cuff in accordance with an embodiment of the present invention to be worn at jointed areas of a user's body.

Referring now to FIG. 11, the cuff 114 includes a cutout portion 115 so that the cuff 114 can be more easily be placed across a jointed region of a user. The cuff 114 includes four or more pressure bladders, 116, 118, 120, and 121. Two of the pressure bladders 116 and 118 are located on the lower portion of the cuff 114 and two bladders 120 and 121 are located on the upper portion. The pressure cuff control unit 112 is similar to pressure cuff control unit 12 as described above with control unit 112 being adapted to drive four bladders. The cutout portion 115 allows the cuff 114 to hinge more easily and provides a break in the hook and loop type fastener strips 164 so that the upper and lower portions of the cuff 114 can be wrapped and adjusted separately.

Figure 12:
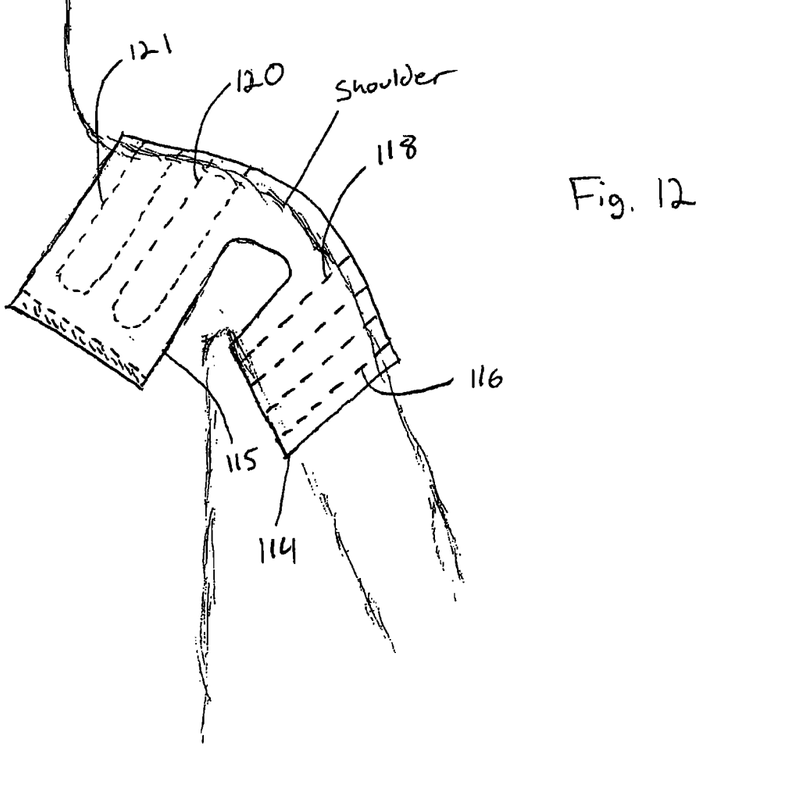
FIG. 12 is a perspective view of the pressure cuff of FIG. 11 on the shoulder of a user according to an embodiment of the present invention.

As shown in FIG. 12, the cuff 114 is placed over a user's shoulder and upper arm region. The distal portion of the cuff 114 containing bladders 116 and 118 is wrapped around the arm and secured in place using the hook and loop type fastener strips 164. The proximal portion of the cuff 114 containing bladders 120 and 121 is laid over the shoulder region wherein the opposite ends of the cuff 114 are not held together with strips 164. The proximal portion of the cuff 114 can be held in place by its own weight or can include a rubberized backing to increase friction so that the cuff 114 stays in place. Additionally, other straps or clips could be used to secure the proximal region of the cuff when it is laid over the shoulder region of the user.

As shown in FIG. 13, the cuff 114 is placed over a user's leg across the knee region. The distal portion of the cuff 114 containing bladders 116 and 118 is wrapped around the leg below the knee and secured in place using the hook and loop type fastener strips 164. The proximal portion of the cuff 114 containing bladders 120 and 121 is wrapped around the leg above the knee and secured in place using the hook and loop type fastener strips 164.

Figure 14:
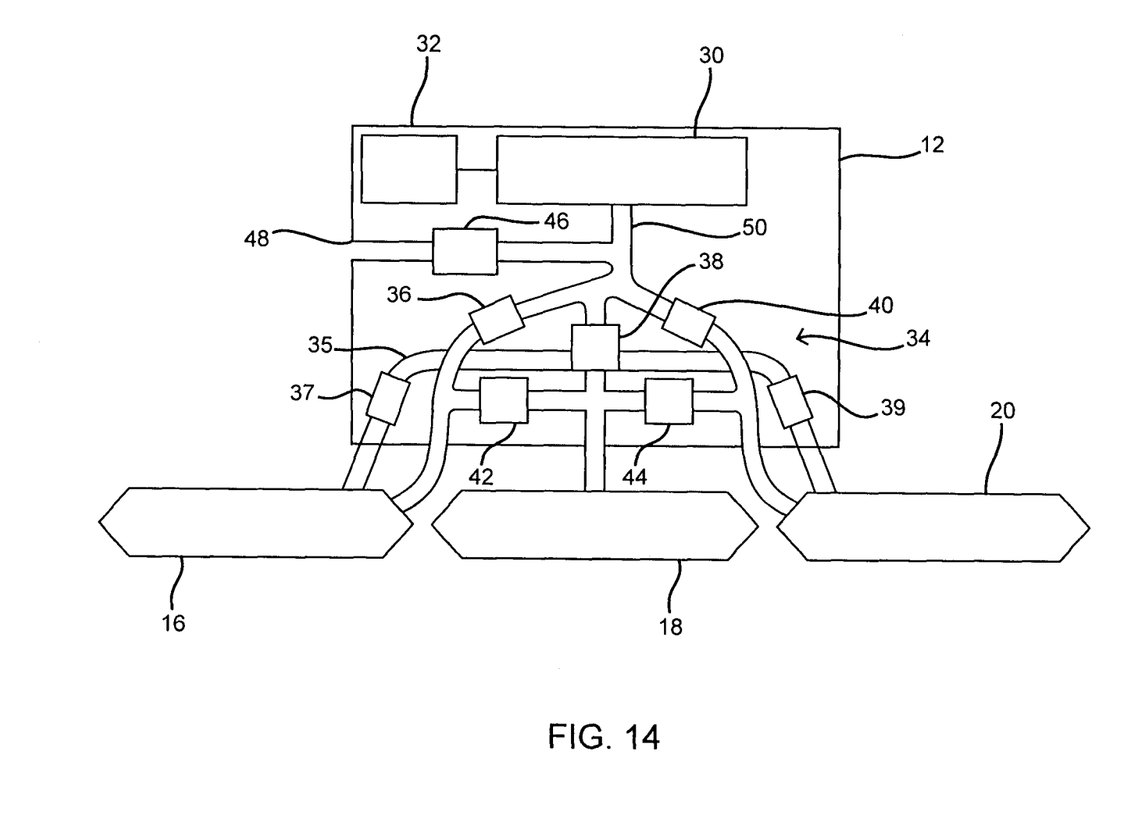
FIG. 14 is a front view of an alternate embodiment of the pressure cuff device that shows an interconnect tube directly connecting the first bladder to the non-adjacent bladder.

FIG. 14 shows a front view of an alternate embodiment of the pressure cuff device 10 that further includes an interconnect tube 35 directly connecting two non-adjacent bladders 16 and 20. The non-adjacent bladder interconnect tube 35 allows the non-adjacent bladders 16 and 20 to be in direct communication such that one of the non-adjacent bladders can be directly inflated by the other non-adjacent bladder. Also located on the non-adjacent bladder interconnect tube 35 are valves 37 and 39 to regulate the fluid communication between the bladders.

Figure 15:
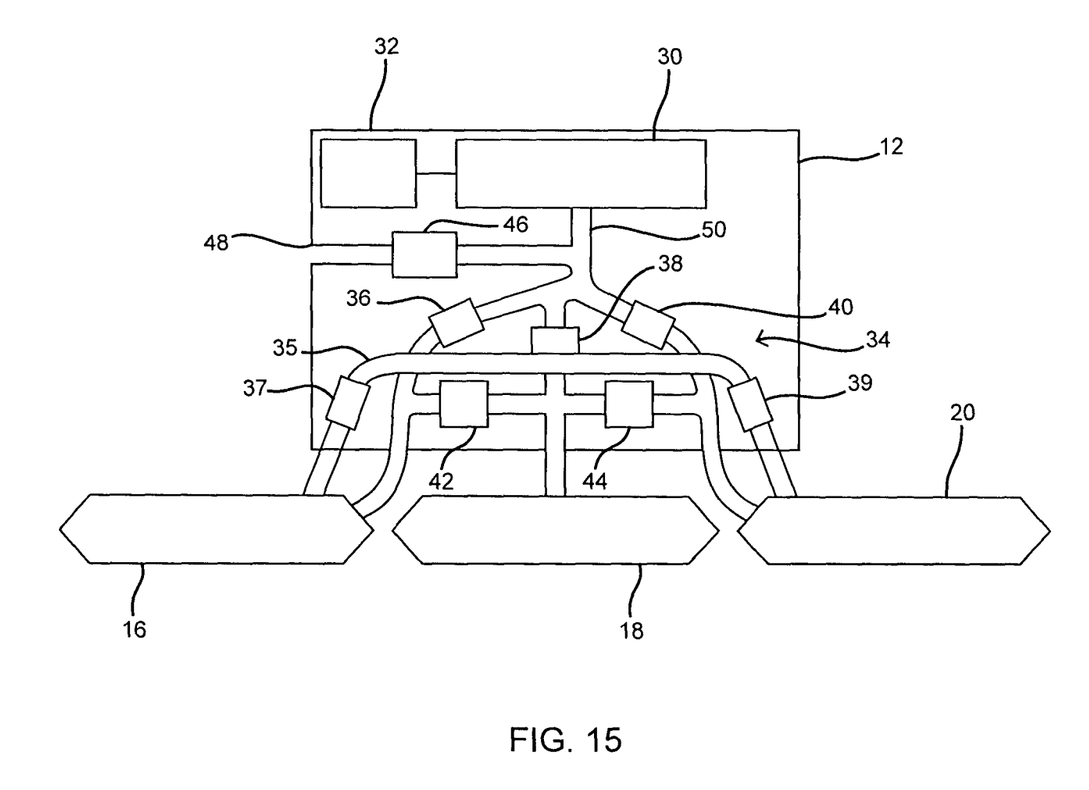
FIG. 15 is a rear view of the pressure cuff device of FIG. 14.

FIG. 15 shows a rear view of the pressure cuff device of FIG. 14.

Figure 16:
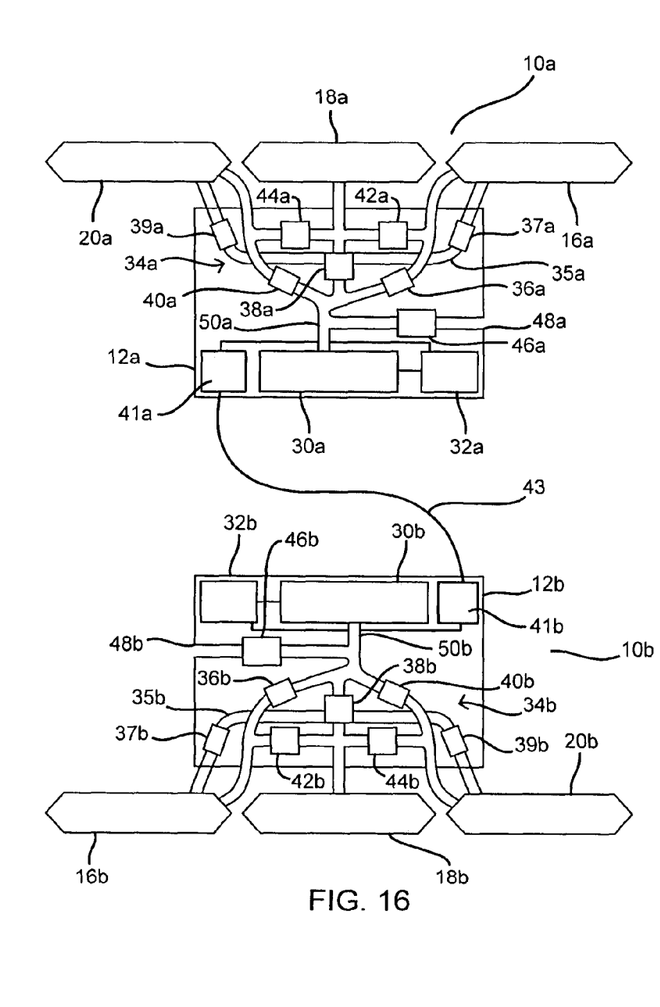
FIG. 16 is a further alternate embodiment of the present invention that shows a first pressure cuff device and a second pressure cuff device each having a communications module and being in communication through a wired connection between the communication modules of the pressure cuff devices.

Shown in FIG. 16 is a view of a first pressure cuff device 10a in electrical communication with a second pressure cuff device 10b for synchronized operation. The pressure cuff devices in this embodiment each further include a communications module 41a and 41b to facilitate the communication between the two pressure cuff devices 10a and 10b. The electrical communication in this embodiment is through a wired connection 43 between the respective communications modules 41a and 41b. The communication modules 41a and 41b in combination with the wired connection 43 place the first pressure cuff device 10a in communication with the second pressure cuff device 10b to synchronize the operation of the pressure cuff devices.

Further, the pressure cuff device 10 can have additional uses. The device 10 can be used in an emergency situation as a tourniquet when a person has suffered trauma. An emergency responder or the injured person can place the cuff around the injured appendage and use the interface to control the device such that all the bladders inflate to a maximum pressure to reduce the loss of blood from a damaged appendage. The device can be preprogrammed with a "tourniquet" profile such that the proper inflation occurs automatically when selected by the user and in emergency situations.

Optionally, the cuff device 10 may include expansion ports and communications modules. The optional expansion ports and communications modules can enable the cuff device 10, for example, to store medical information, and communicate with other medical devices and share medical information, treatment history, etc. The cuff device 10 may optionally include GPS and cellular transceivers, allowing added functionality and capabilities to the cuff device 10.

While the invention has been particularly shown and described with reference to preferred embodiments thereof, it will be understood by those skilled in the art that various changes in form and details may be made therein without departing from the spirit and scope of the invention.

The invention claimed is:

1. A pressure cuff device for stimulating a flow of blood, comprising:
    an adjustable cuff configured to be secured to an appendage of a user;
    an air compressor;
    a plurality of air bladders disposed in the adjustable cuff, each of the plurality of air bladders being connected to the air compressor via a valve-controlled tube;
    a plurality of interconnecting tubes, each interconnecting tube having an interconnect valve and connecting at least two of the valve controlled tubes;
    an air exhaust port having an exhaust valve in fluid communication with each of the valve-controlled tubes; and
    a control module configured to operate the air compressor, the exhaust valve, and each of the valve-controlled tubes so as to inflate and deflate at least one of the plurality of air bladders to at least one predetermined pressure at a predetermined time, wherein said plurality of interconnecting tubes allows at least one of said bladders to be directly inflated by an already inflated air bladder that is not positioned adjacent to said at least one of said bladder to be directly inflated.

2. The pressure cuff device as recited in claim 1, further comprising a control unit, said control unit comprising a housing having a bottom wall, a top wall, and at least one sidewall extending from said bottom wall to said top wall, said housing storing said control module, said exhaust valves and interconnect valves of said pressure cuff device, and at least a portion of said valve controlled tubes and interconnecting tubes of said pressure cuff device therein.

3. The pressure cuff device as recited in claim 1, further comprising a plurality of pressure sensors, each of the plurality of pressure sensors being configured to measure a pressure in each respective air bladder and communicate the measured pressure to the control module.

4. The pressure cuff device as recited in claim 1, wherein each of the plurality of air bladders is disposed in the cuff so that it circumferentially surrounds the appendage when the cuff is secured.

5. The pressure cuff device as recited in claim 1, further comprising at least one electrical contact configured to provide electrical stimulation to the appendage.

6. The pressure cuff device as recited in claim 1, further comprising at least one vibration devices configured to provide a vibration to the appendage.

7. The pressure cuff device as recited in claim 1, further comprising at least one heating element configured to provide heat to the appendage.

8. The pressure cuff device as recited in claim 1, further comprising at least one cooling element configured to cool the appendage.

9. The pressure cuff device as recited in claim 1, wherein the cuff is secured via a hook and loop type fastener mechanism.

10. The pressure cuff device as recited in claim 1, further comprising a power source configured to provide power to at least one of the control module and the air compressor.

11. The pressure cuff device as recited in claim 1, wherein the at least one of the predetermined pressure and the predetermined time are adjustable by the user.

12. The pressure cuff device as recited in claim 1, further comprising a temperature sensor configured to measure a temperature of the cuff device and shut down the cuff device if the measured temperature exceeds a predetermined temperature.

13. The pressure cuff device as recited in claim 1, further comprising a user interface configured to operate the pressure cuff.

14. The pressure cuff device as recited in claim 13, wherein the user interface is configured to enable programming of at least one of an inflation pressure, an inflation speed, and an inflation cycle time associated with at least one of the plurality of air bladders.

15. The pressure cuff device as recited in claim 1, further comprising a remote device configured to operate at least one pressure cuff.

16. The pressure cuff device as recited in claim 1, further comprising a GPS receiver.

17. The pressure cuff device as recited in claim 1, further comprising a cellular transceiver.

18. The pressure cuff device as recited in claim 1, further comprising a communication module to communicate with a second pressure cuff device to synchronize the operation of said pressure cuff device with said second pressure cuff device, said second pressure cuff device also comprising a plurality of air bladders.

19. The pressure cuff device of claim 1 wherein said pressure cuff device is used as a tourniquet.

20. A system for stimulating the flow of blood, comprising:
a first pressure cuff device, comprising:
an adjustable cuff configured to be secured to an appendage of a user;
an air compressor;
a plurality of air bladders disposed in the adjustable cuff, each of the plurality of air bladders being connected to the air compressor via a valve-controlled tube;
a plurality of interconnecting tubes, each interconnecting tube having an interconnect valve and connecting at least two of the valve-controlled tubes;
an air exhaust port having an exhaust valve in fluid communication with each of the valve-controlled tubes; and
a control module configured to operate the air compressor, the exhaust valve, and each of the valve-controlled tubes so as to inflate and deflate at least one of the plurality of air bladders to at least one predetermined pressure at a predetermined time wherein said plurality of interconnecting tubes allows at least one of said bladders to be directly inflated by an already inflated air bladder that is not positioned adjacent to said at least one of said bladder to be directly inflated;
a second pressure cuff device, comprising:
an adjustable cuff configured to be secured to an appendage of a user;
an air compressor;
a plurality of air bladders disposed in the adjustable cuff, each of the plurality of air bladders being connected to the air compressor via a valve-controlled tube;
a plurality of interconnecting tubes, each interconnecting tube having an interconnect valve and connecting at least two of the valve-controlled tubes;
an air exhaust port having an exhaust valve in fluid communication with each of the valve-controlled tubes; and
a control module configured to operate the air compressor, the exhaust valve, and each of the valve-controlled tubes so as to inflate and deflate at least one of the plurality of air bladders to at least one predetermined pressure at a predetermined time, wherein said plurality of interconnecting tubes allows at least one of said bladders to be directly inflated by an already inflated air bladder that is not positioned adjacent to said at least one of said bladder to be directly inflated;
said first pressure cuff device further comprising a first communications module and said second pressure cuff device further comprising a second communications module, said first and second communications modules enabling said first pressure cuff device to communicate with said second pressure cuff device to synchronize the operation between said first and said second pressure cuff devices.

21. A pressure cuff device for stimulating a flow of blood, comprising:
an adjustable cuff configured to be secured to an appendage of a user and having at least a first air bladder, a second air bladder, and a third air bladder disposed therein;
a control unit, said control unit having disposed therein:
a control module,
an air compressor,
said air compressor being in fluid communication with a first tube, said first tube being in fluid communication with at least a first, second and third air bladder tube and said first tube further being in fluid communication with a first exhaust tube member and wherein:
said first air bladder tube connects said first tube with said first air bladder,
said second air bladder tube connects said first tube with said second air bladder, and
said third air bladder tube connects said first tube with said third air bladder,
wherein there is a plurality of interconnecting tubes connecting at least two of said air bladder tubes,
wherein the flow of air from said compressor through said first tube, said air bladder tubes, said plurality of interconnecting tubes, and said first exhaust tube member is controlled by valves on each of said air bladder tubes, interconnecting tubes, and exhaust tube member,
wherein said control module is configured to operate said air compressor and each of said valves in each of said air bladder tubes, interconnecting tubes, and exhaust tube member to inflate and deflate at least one of said air bladders to at least one predetermined pressure at a predetermined time, and
wherein said plurality of interconnecting tubes allow at least one of said air bladders to be directly inflated by an already inflated air bladder that is not positioned adjacent to said bladder to be inflated.

22. A pressure cuff device for stimulating a flow of blood, comprising:
an adjustable cuff configured to be secured to an appendage of a user;
an air compressor;
a plurality of air bladders disposed in the adjustable cuff, each of the plurality of air bladders being connected to the air compressor via a valve-controlled tube between each of said air bladders and said compressor each of said air bladders being further connected to at least one other air bladder by at least one other air bladder by at least one other interconnecting tube, wherein each of said at least one of said interconnecting tubes have an interconnect valve; and
a control module configured to operate the air compressor and control the opening and closing of said interconnect valves such that when a first one of said plurality of air bladders is filled with air at a high pressure, at least a portion of that high pressure air is vented into a second one of said plurality of air bladders that is not adjacent to said first one of said plurality of air bladders by said interconnect valves to thereby change the pressure in a second bladder without operating the compressor.

* * * * *